United States Patent
Mirajkar et al.

(10) Patent No.: US 9,125,860 B2
(45) Date of Patent: Sep. 8, 2015

(54) PHOSPHATE FREE ORAL CARE COMPOSITIONS BASED ON MAGNOLIA ANTIBACTERIAL AGENT

(75) Inventors: Yelloji-Rao K. Mirajkar, Piscataway, NJ (US); Guofeng Xu, Plainsboro, NJ (US); Ying Yang, Monmouth Junction, NJ (US); Thomas Boyd, Metuchen, NJ (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 76 days.

(21) Appl. No.: 13/812,266

(22) PCT Filed: Jul. 29, 2010

(86) PCT No.: PCT/US2010/043645
§ 371 (c)(1),
(2), (4) Date: Jan. 25, 2013

(87) PCT Pub. No.: WO2012/015408
PCT Pub. Date: Feb. 2, 2012

(65) Prior Publication Data
US 2013/0129643 A1    May 23, 2013

(51) Int. Cl.
*A61K 36/575*     (2006.01)
*A61Q 11/00*      (2006.01)
*A61K 8/97*       (2006.01)
*A61K 8/27*       (2006.01)
*A61K 31/05*      (2006.01)

(52) U.S. Cl.
CPC . *A61K 31/05* (2013.01); *A61K 8/27* (2013.01); *A61K 8/97* (2013.01); *A61K 36/575* (2013.01); *A61Q 11/00* (2013.01); *A61K 2300/00* (2013.01)

(58) Field of Classification Search
USPC ................................... 424/49, 58
See application file for complete search history.

(56) References Cited

U.S. PATENT DOCUMENTS

| | | |
|---|---|---|
| 4,656,031 A | 4/1987 | Lane et al. |
| 5,037,635 A | 8/1991 | Nabi et al. |
| 6,403,059 B1 | 6/2002 | Martin et al. |
| 6,500,409 B1 | 12/2002 | Scherl et al. |
| 7,347,985 B2 | 3/2008 | Maxwell et al. |
| 7,632,525 B2 | 12/2009 | Dodds et al. |
| 8,071,077 B2 | 12/2011 | Subramanyam et al. |
| 8,303,939 B2 | 11/2012 | Castellana et al. |
| 2005/0036959 A1 | 2/2005 | Ibrahim et al. |
| 2005/0175552 A1 | 8/2005 | Hoic et al. |
| 2005/0210615 A1 | 9/2005 | Shastry et al. |
| 2006/0127329 A1 | 6/2006 | Xu et al. |
| 2006/0134024 A1 | 6/2006 | Trivedi et al. |
| 2006/0140885 A1 | 6/2006 | Gaffar et al. |
| 2007/0020201 A1 | 1/2007 | Boyd et al. |
| 2007/0041914 A1 | 2/2007 | Gaffar et al. |
| 2009/0087501 A1 | 4/2009 | Cummins |

FOREIGN PATENT DOCUMENTS

| | | |
|---|---|---|
| CN | 1318362 | 10/2001 |
| CN | 1723011 | 1/2006 |
| CN | 101227883 | 7/2008 |
| JP | S57-85319 | 5/1982 |
| JP | H01-151512 | 6/1989 |
| JP | H08-175946 | 7/1996 |
| JP | H11-228368 | 8/1999 |
| JP | 2008-115115 | 5/2008 |
| WO | WO 9426245 A1 * | 11/1994 |
| WO | WO 01/82922 | 11/2001 |
| WO | WO 2006/065403 | 6/2006 |
| WO | WO 2006/071653 | 7/2006 |
| WO | WO 2007/013937 | 2/2007 |
| WO | WO 2009/140577 | 11/2009 |

OTHER PUBLICATIONS

Toxicology Data Network. Sodium Lauryl Sulfoacetate. Date Retrieved: Jun. 30, 2014. p. 12 out of 14.*
Ripa et al., 1990, "Clinical study of the anticaries efficacy of three fluoride dentifrices containing anticalculus ingredients: three-year (final) results," J. Clinical Dentistry 2(2):29-33.
Lee et al., (Apr. 2005), "Anti-Inflammatory Effects of Magnolol and Honokiol are Mediated through Inhibition of the Downstream Pathway of MEKK-1 in Nf-κB Activation Signaling," Planta. Med. 71(4):338-43.
Lin et al., (2007), "Effects of honokiol and magnolol on acute and inflammatory pain models in mice," Life Sciences 81: pp. 1071-1078.
Park et al., (2004), "In vitro antibacterial and anti-inflammatory effects of honokiol and magnolol against *Propionibacterium* sp.," European Journal of Pharmacology 496: pp. 189-195.
International Search Report and Written Opinion of the ISA issued for corresponding International Patent Application No. PCT/US2010/043645, mailed Apr. 14, 2011.
Written Opinion Of The International Preliminary Examining Authority, Jul. 19, 2012, Colgate-Palmolive Company.

* cited by examiner

*Primary Examiner* — Frederick Krass
*Assistant Examiner* — Tracy Liu
(74) *Attorney, Agent, or Firm* — Howard C. Lee

(57) ABSTRACT

An oral care composition for treating or preventing calculus comprising an anticalculus agent and an antibacterial agent comprising a biphenol compound obtainable from *Magnolia officinalis*, wherein the composition is free of phosphate-containing anticalculus agents.

7 Claims, No Drawings

PHOSPHATE FREE ORAL CARE COMPOSITIONS BASED ON MAGNOLIA ANTIBACTERIAL AGENT

The present invention relates to oral care compositions and methods employing such compositions for use in treating or preventing calculus formation.

BACKGROUND

Dental plaque is a soft deposit which forms on the surfaces of teeth. Dental plaque is generally believed to be formed as a byproduct of bacterial growth and comprises a dense microbial layer consisting of a mass of microorganisms embedded in a polysaccharide matrix. Plaque tenaciously adheres to the surfaces of teeth, especially along irregular and rough surfaces, and is typically found at the gingival margin, in cracks in the enamel, and on the surface of built-up dental calculus.

Gingivitis is the inflammation or infection of the gums and the alveolar bones that support the teeth. Gingivitis is generally believed to be caused by bacteria in the mouth (particularly the bacteria instigated in plaque formation) and the toxins formed as byproducts from the bacteria. Periodontitis is generally believed to occur where unremoved plaque hardens into calculus (tartar) which affects the periodontal ligaments. Periodontitis is a progressively worsened state of disease as compared to gingivitis. As plaque and calculus continue to build up, the gums begin to recede from the teeth and pockets form therebetween, which ultimately may result in destruction of the bone and periodontal ligament. These reactions lead to the destruction of the supporting structure, continued infection, and potentially the subsequent loss of teeth.

The plaque formed along the tooth surfaces thus provides a locus for calculus (tartar) formation. Dental calculus, or tartar, is a hard mineralized solid formed on the teeth when crystals of calcium phosphate are deposited in the pellicle and extracellular matrix of the dental plaque and become crystalline hydroxyapatite, sufficiently closely packed together for the aggregates to become resistant to deformation. Regular brushing aids in preventing a rapid build-up of these deposits, but even regular brushing is not sufficient to remove all of the calculus deposits which adhere to the teeth. While there is no complete agreement on the route by which precipitated calcium and orthophosphate ultimately become the crystalline material called hydroxyapatite (HAP), it is generally agreed that at higher saturations (above the critical saturation limit) the precursor to crystalline HAP is an amorphous or microcrystalline calcium phosphate. "Amorphous calcium phosphate" although related to hydroxyapatite differs from it in atomic structure, particle morphology, and stoichiometry. Agents which effectively interfere with crystalline growth of HAP will be effective as anticalculus agents. One suggested mechanism by which many anticalculus agents inhibit calculus formation involves an increase of the activation energy barrier thus inhibiting the transformation of precursor amorphous calcium phosphate to HAP. Studies have shown that there is a good correlation between the ability of a compound to prevent HAP crystalline growth in vitro and its ability to prevent calcification in vivo, provided that the compound is stable in and inert to other components in an oral care composition and to saliva in the oral cavity.

Thus, it is desirable to have an oral care composition that combats plaque by antibacterial activity and further controls and prevents calculus formation. It is difficult to predict the antiplaque efficacy of antibacterial compounds when incorporated in a delivery vehicle and particularly in oral compositions having other active ingredients, such as anticalculus (tartar control) agents. There is often a negative interaction between an antibacterial agent with other active ingredients or other components in a delivery vehicle of an oral care composition that reduces the effective performance of such compositions, including toothpaste and mouth rinses. This is especially true for many anticalculus systems.

In order to overcome these problems a tartar control oral care composition has hitherto been provided which contains an antibacterial active compound from an extract of *magnolia* and an anticalculus system comprising tetrasodium pyrophosphate and sodium tripolyphosphate. Active compounds extracted from *magnolia* include magnolol and honokiol which are antibacterial biphenol compounds. Tetrasodium pyrophosphate and sodium tripolyphosphate are anticalculus agents.

Notwithstanding the efficacy of certain antibacterial agents, there is a continuing interest in the oral care field for oral care compositions which improve the treatment of both plaque and tartar formation. Thus, there is a need for a highly effective antibacterial, antiplaque and anticalculus oral care composition to prevent or diminish oral care diseases.

SUMMARY

In a first aspect, the present invention provides an oral care composition for treating or preventing calculus, which composition comprises an anticalculus agent and an antibacterial agent comprising a biphenol compound obtainable from *Magnolia officinalis*, wherein the composition is free of phosphate-containing anticalculus agents.

The present invention further provides an oral care composition for use in treating or preventing calculus and plaque, which composition comprises an anticalculus agent and an antibacterial agent comprising a biphenol compound obtainable from *Magnolia officinalis*; wherein the composition is free of phosphate-containing anticalculus agents.

In a further aspect, the present invention provides a method of preventing inhibition of oral uptake of an antibacterial biphenol compound obtainable from *Magnolia officinalis* from an anticalculus oral care composition, which comprises formulating the oral care composition with the antibacterial biphenol compound and an anticalculus agent which is phosphate-free.

There is further provided use of a phosphate-free anticalculus agent in the manufacture of an anticalculus oral care composition comprising an antibacterial biphenol compound obtainable from *Magnolia officinalis*, for preventing inhibition of uptake of the antibacterial biphenol compound.

In a further aspect, the present invention provides a method for treating or preventing calculus formation in the oral cavity, which comprises contacting the oral cavity with an oral care composition comprising an anticalculus agent and an antibacterial agent comprising a biphenol compound obtainable from *Magnolia officinalis*, wherein the oral care composition is free of phosphate-containing anticalculus agents.

It has surprisingly been found that, in oral care compositions which comprise an antibacterial biphenol compound obtainable from an extract of *magnolia* together with an anticalculus system comprising tetrasodium pyrophosphate and/or sodium tripolyphosphate, replacement of the phosphate-containing anticalculus agents with an anticalculus agent which is phosphate-free provides significantly improved delivery of the biphenol compound. It has been found that phosphate-containing anticalculus agents such as tetrasodium pyrophosphate and sodium tripolyphosphate appear to inhibit uptake of antibacterial biphenoyl compounds.

Accordingly, by ensuring that the oral care compositions of the present invention are free of phosphate-containing anticalculus agents, inhibition of oral uptake is prevented. In this way, delivery of the antibacterial biphenol compounds is significantly improved thereby allowing increase in antiplaque activity of the oral composition or enabling a reduction in the amount of the antibacterial biphenol compound needed to achieve antiplaque activity.

The oral care compositions of the present invention are free of phosphate-containing anticalculus agents and in certain embodiments free of phosphates or polyphosphates, typically at least to the extent that delivery of the biphenol compound is reduced by no more than 20%, no more than 10%, or no more than 5% as compared with a control oral care composition containing no phosphate. Delivery of the biphenol compound is typically measured using a model system of delivery to saliva-coated hydroxyapatite discs, as described in further detail below. As used herein, the term "phosphate" denotes phosphates and polyphosphates including pyrophosphates. Oral care compositions according to the invention must be free at least of tetrasodium pyrophosphate.

The antibacterial agent of the present invention, a "*Magnolia* antibacterial agent", comprises a biphenol compound obtainable, derived or developed from *Magnolia officinalis*, for example as an extract therefrom. As referred to herein, such an "extract" of *magnolia* is an extract from dried cortex, or bark, of a plant from the Magnoliaceae family, such as *Magnolia officinalis*, (herein "*magnolia*") or a synthetic or semi-synthetic equivalent of such an extract or an active component thereof. Additionally, the agent may be developed from *Magnolia officinalis*, such as a synthetic magnolol, honokiol, tetrahydromagnolol, tetrahydrohonokiol, propylmagnolol, propylhonokiol, isopropylmagnolol, isopropylhonokiol, butylmagnolol, or butylhonokiol which have demonstrated bactericidal properties against representative oral bacteria *S. mutans, F. nucleatum, V. parvula, A. naslundii, P. gingivitis* in the in vitro test Minimal Inhibitory Concentration (MIC). In certain embodiments of the present invention, the antibacterial ingredient in the active composition comprises one or more active compounds that have been isolated from an extract of *magnolia*. In other embodiments, the antibacterial ingredient comprises an extract of *magnolia*. In certain embodiments, extracts of *Magnolia* Cortex (the bark of *Magnolia officinalis*) contain active compounds including: magnolol, honokiol, tetrahydromagnolol, and tetrahydrohonokiol, which have demonstrated bactericidal properties against representative oral bacteria *S. mutans, F. nucleatum, V. parvula, A. naslundii, P. gingivitis* in the in vitro test Minimal Inhibitory Concentration (MIC). It should be noted that any plant from the Magnoliaceae family is suitable for the present invention and may be used in alternative embodiments. In certain embodiments the extract comprises an antimicrobially effective concentration of a compound selected from the group consisting of magnolol, honokiol, tetrahydromagnolol, tetrahydrohonokiol, propylmagnolol, propylhonokiol, isopropylmagnolol, isopropylhonokiol, butylmagnolol, butylhonokiol and mixtures thereof.

As used herein, "extracting" or "extraction" of a solid or liquid material means contacting the material with an appropriate material, such as a solvent to remove the substance(s) desired to be extracted from the material. Such an extraction may be carried out by conventional means known to one of skill in the art, for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such as by filtration or by settling and decanting.

In one embodiment of the present invention, the *magnolia* extract is isolated by supercritical fluid extraction (SFE) using carbon dioxide (CO2).

In various embodiments, the active antibacterial ingredient comprises either magnolol, honokiol, or both. Magnolol and honokiol are non-ionic hydroxybiphenyl compounds, the structures of which are represented as follows:

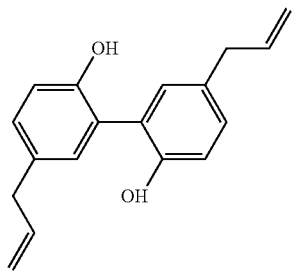

Magnolol

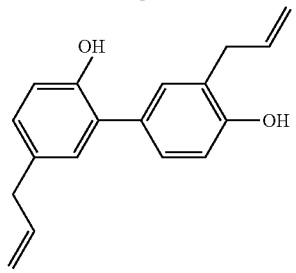

Honokiol

Additionally, tetrahydromagnolol and tetrahydrohonokiol are hydrogenated analogs of magnolol and honokiol often found in relatively small concentrations in the extracts of *magnolia*, and as such may be included in the antibacterial ingredient.

These compounds and their extraction from *magnolia* are described in further detail in WO2006/065403.

In various embodiments of the present invention, the oral care composition shall include a safe and effective amount of the biphenol compound from *magnolia*. Accordingly, the amount of compound is to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific safe and effective amount of the compound will vary with such factors as the particular condition being treated, the physical condition of the subject, the nature of concurrent therapy (if any), the specific compound used, the specific dosage form, the carrier employed, and the desired dosage regimen.

Additionally, the concentration the biphenol compound in the oral care composition will vary depending on delivery form, dosage regimen, end benefits, pathology, and/or the individual therapeutic requirements of the subject(s) to whom it is admitted depends upon the relative concentration of the active compounds in the extract, and as such, it is contemplated that the amount of biphenol compound present may vary as recognized by one of skill in the art. Additionally, the concentration of the active ingredients is typically dependent upon the form of the oral composition. For example, mouthrinses typically have a relatively low concentration of an active ingredient, as where dentifrices have a higher concentration to achieve the same delivered dosage based on ease of dispersion. Likewise, confectionary compositions typically have a relatively high concentration of active ingredient to enable sufficient dispersion as they dissolve or are masticated.

In various embodiments of the present invention, active compound(s) from *magnolia* may be present in the oral care composition in a concentration of about 0.001 to about 10% by weight. In one embodiment, it is present in the oral care composition in a concentration of about 0.01 to about 3% by weight. In other embodiments, it is present at less than 1%, for example the extract is at a concentration of about 0.01 to about 1% by weight. In one embodiment, the compound is present in the oral care composition at a concentration of about 0.5%. In another, the compound is present in the oral care composition at a concentration of about 1%.

In certain embodiments of the present invention, additional antibacterial ingredients may be included in the oral care compositions. If added, the antibacterial active ingredients it is desirable that the additive does not substantially detract from the efficacy and bioavailability of the tartar control agents or the active compound of the extract. In certain embodiments, the additional antibacterial active ingredients are nonionic. Some additional antibacterial agents are described in WO2006/065403.

The anticalculus agent enables the oral composition to inhibit, treat or prevent calculus formation. This agent in certain embodiments comprises a zinc ion source. The zinc ion source for the oral care composition of the invention may be any source known or developed in the art or any combination or mixture of such sources. For example, any zinc salt and/or compound may be employed as zinc ion source and such zinc ion source, including water soluble and insoluble, organic and inorganic zinc salts. Examples of suitable zinc compounds that may be employed include, but are not limited to, zinc acetate, zinc acetylacetonate, zinc ammonium sulfate, zinc benzoate, zinc bromide, zinc beryllium orthosilicate, zinc borate, zinc butylphthalate, zinc butylxanthate, zinc caprylate, zinc carbonate, zinc chloroanilate, zinc chlorate, zinc chromate, zinc citrate, zinc cyclohexanebutyrate, zinc chloride, zinc gallate, zinc fluoride, zinc alpha-glucoheptonate, zinc gluconate, zinc glycerophosphate, zinc hydroxide, zinc 8-hydroxyquinoline, zinc 12-hydroxystearate, zinc iodide, zinc acrylate, zinc oxide, zinc propionate, zinc isovalerate, zinc D-lactate, zinc DL-lactate zinc laurate, zinc hexafluorosilicate, zinc methacrylate, zinc molybdate, zinc naphthenate, zinc octoate, zinc oleate, zinc phenolsulfonate, zinc pyridine-2-thiol-1-oxide, zinc resinate, zinc salicylate, zinc sulfate, zinc nitrate, zinc selenide, zinc stearate, zinc sulfanilate, zinc tartrate, zinc tellurate, zinc tungstate, zinc valerate, zinc vanadate, zinc tribromosalicylanilide, and zinc ricinoleate. In certain embodiments, zinc oxide may be used as zinc ion source of the oral care composition.

It has been found that, in contrast to phosphate containing anticalculus agents, anticalculus agents which comprise a zinc ion source do not inhibit uptake of biphenol compounds such as magnolol. In fact, if anything, the addition of a zinc ion source such as zinc oxide to compositions according to the present invention improves the delivery of the biphenol compound.

Typically, these zinc ion sources may be added in an amount which is up to 2% by weight. In one embodiment, 0.5% by weight of zinc ion source is added. In another embodiment, 1% by weight of zinc ion source is added. The zinc ion source may be added in the form of non-aggregated nanoparticles as described in WO2007/013937.

Oral care compositions according to the invention may include orally acceptable carrier components which are generally well known in the art. Such components may be selected from at least one of the following: surfactants, humectants, thickeners, foaming agents, a fluoride ion source, flavourings, colours, chelating agents, polymers, enzymes, water, actives, sweeteners, preservatives, diluents and other materials. Typical examples of each of these components are described in further detail in WO2009/140577, for example.

In certain embodiments, a surfactant is included in the oral care composition because this may assist in solubilising the antibacterial biphenol compound. In common with other carrier components, in certain embodiments, the surfactant should be phosphate-free. Useful surfactants include anionic surfactants such as the water-soluble salts of alkyl sulfates having 10 to 18 carbon atoms in the alkyl radical and the water-soluble salts of sulfonated monoglycerides of fatty acids having 10 to 18 carbon atoms. Sodium lauryl sulfates, sodium lauroyl sarcosinate and sodium coconut monoglyceride sulfonates are examples of anionic surfactants of this type. Sodium lauryl sulfate (SLS) is selected in certain embodiments.

The specific composition of the orally-acceptable carrier will depend upon the intended use of the composition. The carrier can be a liquid, semi-solid or solid phase. The oral care compositions can be in the form of a dentifrice such as a toothpaste, toothpowder, prophylaxis paste or gel, typically intended for cleaning a hard surface within the oral cavity. A dentifrice may include further optional ingredients such as adhesives, sudsing agents and abrasives. Such components are described in further detail in WO2009/140577.

The oral care composition may alternatively be in the form of a mouthrinse such as a mouthwash, spray or rinse which is substantially liquid in character. Further details of mouthrinse compositions may be found in WO2006/065403.

The oral care composition of the present invention can be made by any of the methods known in the art for combining ingredients to make oral care compositions. Examples of methods that can be used are set forth in, e.g., U.S. Pat. No. 6,403,059 to Martin et al.; Clinical Pharmacology for Dental Professionals (Mosby-Year Book, Inc., 3rd ed. 1989); Mosby's Dental Hygiene: Concepts, Cases and Competencies, (Daniel, S. and Harfst, S. eds., Elsevier Science Health Science Div. 2002); and Ernest W. Flick, Cosmetic and Toiletry Formulations, 2nd ed.

The oral care composition may also be in the form of a confectionary composition such as a chewing gum, orally soluble tablet, bead or lozenge. Further details of such confection compositions may be found in WO2006/065403.

The present invention provides methods and processes for using the oral care compositions as described herein to clean and/or treat oral surfaces, especially tooth surfaces. The oral care compositions may be used to treat and/or inhibit oral conditions such as dental plaque, dental calculus, gingivitis and periodontitis. The compositions may be applied to the subject in any suitable manner known in the art such as, for example, by introducing the composition to the subjects oral cavity using a suitable applicator or delivery device such as a brush, dental strip, film, syringe, tape, pill or any other applicator or delivery device known in the art. Typically, the oral compositions may be repeatedly applied to the subject over a number of days according to a particular treatment schedule. Instructions setting out such a schedule may be provided in commercial packaging with the product.

DETAILED DESCRIPTION

The present invention will now be described in further detail, by way of example only with reference to the following Examples. All percentages given are by weight of the composition unless otherwise indicated.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

In the Examples that follow various formulae are tested for their ability to deliver magnolol to saliva coated hydroxyapatite disks. The disks may be obtained from Clarkson Chromatography Products Inc. Uptake to the disks is determined as follows. All procedures are performed under room temperature, unless otherwise specified. All uptake experiments require sample analysis in triplicate.

Paraffin® stimulated whole saliva is collected from healthy male or female subjects. Saliva supernatant is obtained by centrifuging whole saliva for 10 minutes at 10,000 RPM. Hydroxyapatite (HAP) disks are incubated with 1 ml saliva supernatant in a 15 ml Falcon® tube overnight in a 37° C. shaking water bath to develop a pellicle. Dentifrice slurry is obtained by dissolving dentifrice in distilled water at 1:2 ratio by weight. The dentifrice and water mixture is stirred continuously for at least 30 minutes to ensure the mixture is homogenous. Saliva supernatant is aspirated and 1 ml of dentifrice slurry is added to the same Falcon® tube. The saliva coated HAP disks are treated with dentifrice slurry for 15-30 minutes in a 37° C. shaking water bath. Dentifrice slurry is aspirated and the HAP disks are rinsed with 5 ml of distilled $H_2O$ (Millipore®) and vortexed for 5 seconds. The $H_2O$ is aspirated and the rinsing is repeated once. The treated HAP disk is transferred to a new 15 ml Falcon® tube with 2 ml of 100% ethanol. The Falcon® tube is vortexed for 15 seconds to ensure the active substance is fully extracted off the disk. Ethanol solution is then transferred into a 1 ml standard HPLC vial for analysis. Quantitative HPLC is performed by comparison with suitable standard solutions and the concentration of active substance on the disk is determined.

EXAMPLES

Below are examples of oral care compositions. The compositions comprise an anticalculus agent and a *Magnolia* antibacterial agent, wherein the composition is free of phosphate-containing anticalculus agents. The other materials in the formulations are present for other functions that can be obtained from an oral care composition and do not necessarily change the inventive combination of the anticalculus agent, which is free of phosphate-containing anticalculus agents, and the *Magnolia* antibacterial agent.

Example 1

Compositions of formulae that contain 0.5% Magnolol with tartar salt TSPP (tetrasodium pyrophosphate) (added for tartar benefit), shown in Table 1, were used to test the impact of the salt on the delivery of magnolol on to saliva coated hydroxyapatite disks.

TABLE 1

| Ingredient | Formula 1 | Formula 2 | Formula 3 | Formula 4 |
|---|---|---|---|---|
| Glycerin | 12 | 12 | 12 | 12 |
| Propylene Glycol | 3 | 3 | 3 | 3 |
| Sodium Saccharine | 0.4 | 0.4 | 0.4 | 0.4 |
| Sodium Fluoride | 0.243 | 0.243 | 0.243 | 0.243 |
| Sorbitol | 27.45 | 27.45 | 27.45 | 27.45 |
| DI water | Q.S. | Q.S. | Q.S. | Q.S. |
| Sodium Hydroxide | 0.7 | 0.7 | 0.7 | 0.7 |
| TSPP | 0.5 | 1 | 2 | 0 |
| Flavor | 1 | 1 | 1 | 1 |
| SLS Powder | 1.2 | 1.2 | 1.2 | 1.2 |
| Magnolol | 0.5 | 0.5 | 0.5 | 0.5 |
| Total, wt | 100 | 100 | 100 | 100 |

Results from magnolol uptake, shown in Table 2, suggest that delivery is significantly affected in the presence of tartar salt. For example, while control dentifrice (Formulas 4 containing no TSPP) provided the delivery of 68.50 ppm magnolol, the delivery was only 24.77 ppm with additional presence of 0.5% TSPP (formula 1). Similar results of compromised delivery in the presence of 1% TSPP (Formula 2) and 2% TSPP (Formula 3) were observed.

TABLE 2

| | | Mean uptake, ppm |
|---|---|---|
| 0.5% Magnolol + 0.5% TSPP | Formula 1 | 24.77 |
| 0.5% Magnolol + 1% TSPP | Formula 2 | 26.27 |
| 0.5% Magnolol + 2% TSPP | Formula 3 | 22.50 |
| 0.5% Magnolol + 0% TSPP | Formula 4 | 68.50 |

Example 2

Compositions of complete dentifrices that contain 0.5% magnolol with tartar salt TSPP or Zinc salts (added for tartar benefit), shown in Table 3, were used to test the impact of the salt on the delivery of magnolol on to saliva coated hydroxyapatite disks.

TABLE 3

| Ingredient, % | Formula 5 | Formula 6 | Formula 7 | Formula 8 |
|---|---|---|---|---|
| Sodium CMC | 0.65 | 0.65 | 0.65 | 0.65 |
| Na saccharine | 0.27 | 0.27 | 0.27 | 0.27 |
| Water - DI | Q.S. | Q.S. | Q.S. | Q.S. |
| Sodium fluoride | 0.243 | 0.243 | 0.243 | 0.243 |
| Tetra Sodium Pyrophosphate | 0 | 0.5 | 0 | 0.5 |
| Titanium Dioxide | 0.75 | 0.75 | 0.75 | 0.75 |
| Sorbitol | 54 | 54 | 54 | 54 |
| PEG 600 | 3 | 3 | 3 | 3 |
| Silica High Cleaning | 10 | 10 | 10 | 10 |
| Silica Thickener | 2.75 | 2.75 | 2.75 | 2.75 |
| Silica Abrasiva | 10 | 10 | 10 | 10 |
| Flavor | 1.15 | 1.15 | 1.15 | 1.15 |
| Magnolol | 0.5 | 0.5 | 0.5 | 0.5 |
| Sodium lauryl sulfate | 1.5 | 1.5 | 1.5 | 1.5 |
| Coco Amido Propyl Betaine | 1.25 | 1.25 | 1.25 | 1.25 |
| Zinc Oxide Powder | 0.5 | 0.5 | 1 | 1 |
| Total | 100 | 100 | 100 | 100 |

Results from magnolol uptake, shown in Table 4, suggest that delivery is significantly affected in the presence of tartar salt. For example, while control dentifrice (Formula 5 containing only 0.5% zinc salt) provided the delivery of 63.23 ppm magnolol, the delivery was only 25.96 ppm with additional presence of 0.5% TSPP (formula 6). Similar results of compromised delivery in the presence of 0.5% TSPP was observed when the dentifrices were formulated with 1% Zinc oxide (Formulae 7 and 8).

TABLE 4

| Dentifrice | | Mean uptake, ppm |
|---|---|---|
| 0.5% Magnolol + 0.5% ZnO | Formula 5 | 63.23 |
| 0.5% Magnolol + 0.5% ZnO + 0.5% TSPP | Formula 6 | 25.96 |
| 0.5% Magnolol + 1.0% ZnO | Formula 7 | 65.71 |
| 0.5% Magnolol + 1.0% ZnO + 0.5% TSPP | Formula 8 | 27.98 |

Example 3

Compositions of complete dentifrices that contain 0.5% and 1% magnolol were also tested. Additionally, addition of Zinc salts (added for tartar benefit) with and without sodium sulfate, formulas shown in Table 5, were tested to assess the impact of the zinc salt on the delivery of magnolol on to saliva coated hydroxyapatite disks.

TABLE 5

| Ingredients, % | Formula 9 | Formula 10 | Formula 11 | Formula 12 | Formula 13 |
|---|---|---|---|---|---|
| Glycerin | 20 | 20 | 20 | 20 | 20 |
| Sodium CMC | 1.1 | 1.1 | 1.1 | 1.1 | 1.1 |
| Iota Carrageenan | 0,4 | 0.4 | 0.4 | 0.4 | 0.4 |
| Titanium Dioxide | 0.5 | 0.5 | 0.5 | 0.5 | 0.5 |
| Sorbitol | 19.45 | 19.45 | 19.45 | 19.45 | 19.45 |
| Water | Q.S. | Q.S. | Q.S. | Q.S. | Q.S. |
| Sodium Saccharin | 0.3 | 0.3 | 0.3 | 0.3 | 0.3 |
| Sodium Fluoride | 0.243 | 0.243 | 0.243 | 0.243 | 0.243 |
| Silica High Cleaning | 10 | 10 | 10 | 10 | 10 |
| Silica Abrasiva | 8.5 | 8.5 | 8.5 | 8.5 | 8.5 |
| Silica Thickener | 3 | 3 | 3 | 3 | 3 |
| Zinc Oxide Powder | 0 | 0 | 1 | 0 | 1 |
| Sodium Sulfate | 0 | 0 | 0 | 0.77 | 0.77 |
| Sodium lauryl sulfate | 1.5 | 1.5 | 1.5 | 1.5 | 1.5 |
| Propylene Glycol | 1 | 1 | 1 | 1 | 1 |
| Magnolol | 0.5 | 1 | 1 | 1 | 1 |
| Flavor | 1 | 1 | 1 | 1 | 1 |
| Total | 100 | 100 | 100 | 100 | 100 |

Results from magnolol uptake, also shown in Table 6, suggest that increase in magnolol from 0.5% to 1% increases magnolol delivery slightly. When Zinc oxide was also added to the formula, delivery of Magnolol is further slightly improved. For example, while dentifrice containing no zinc salt (Formula 10) provided the delivery of 75.89 ppm magnolol, the delivery was 89.04 ppm with 1% Zinc oxide (Formula 11). While the addition of sodium sulfate alone (Formula 12) did not impact magnolol delivery, such delivery was slightly improved in the presence of Zinc oxide (Formula 13).

TABLE 6

| Dentifrice | | Mean uptake, ppm |
|---|---|---|
| 0.5% Magnolol | Formula 9 | 67.06 |
| 1% Magnolol | Formula 10 | 75.89 |
| 1% Magnolol + 1% ZnO | Formula 11 | 89.04 |
| 1% Magnolol + 0.77% Na$_2$SO$_4$ | Formula 12 | 75.39 |
| 1% Magnolol + 0.77% Na$_2$SO$_4$ + 1% ZnO | Formula 13 | 82.22 |

Example 4

Compositions of complete dentifrices that contain 1.0% magnolol with higher sodium lauryl sulfate (SLS) (formulas shown in Table 7) were also tested to assess the effect of Zinc salts (added for tartar benefit) on the delivery of magnolol on to saliva coated hydroxyapatite disks.

TABLE 7

| Ingredients % | Formula 14 | Formula 15 | Formula 16 |
|---|---|---|---|
| Glycerin | 18 | 18 | 18 |
| Sodium carboxymethylcellulose (CMC) | 1.1 | 1.1 | 1.1 |
| Iota Carrageenan | 0.4 | 0.4 | 0.4 |
| Titanium Dioxide | 0.5 | 0.5 | 0.5 |
| Sorbitol | 17.8 | 17.8 | 17.8 |
| Water | Q.S. | Q.S. | Q.S. |
| Sodium Saccharin | 0.3 | 0.3 | 0.3 |
| Sodium Fluoride | 0.243 | 0.243 | 0.243 |
| Sodium Sulfate | 0.77 | 0.77 | 0.77 |
| Silica High Cleaning | 10 | 10 | 10 |
| Silica Abrasive | 8.5 | 8.5 | 8.5 |
| Silica Thickener | 3 | 3 | 3 |
| Zinc Oxide Powder | 0 | 0.5 | 1 |
| Sodium lauryl sulfate | 1.8 | 1.8 | 1.8 |
| Polyethylene Glycol 600 | 2 | 2 | 2 |
| Magnolol | 1 | 1 | 1 |
| Flavor | 1 | 1 | 1 |
| Total | 100 | 100 | 100 |

Magnolol uptake results shown in Table 8 suggest that the delivery is almost parity in the presence of zinc oxide.

TABLE 8

| Dentifrice | | Mean uptake, ppm |
|---|---|---|
| 1.8% SLS + 1.0% Magnolol | Formula 14 | 117.28 |
| 1.8% SLS + 1.0% Magnolol + 0.5% ZnO | Formula 15 | 115.79 |
| 1.8% SLS + 1.0% Magnolol + 1.0% ZnO | Formula 16 | 104.42 |

Taken together the results indicate that a biphenol compound obtainable from *Magnolia officinalis* such as magnolol is subject to significant inhibition of delivery to a tooth surface model in the presence of a phosphate-containing anticalculus agent such as tetrasodium pyrophosphate. By making the compositions phosphate-free this inhibition is not observed. Replacing the phosphate containing anticalculus agent with a phosphate-free anticalculus agent such as a zinc salt provides an oral care composition which has anticalculus properties and enhanced uptake of the antibacterial component. The zinc salt is found to improve the delivery of the biphenol compound.

The invention claimed is:
1. An oral care composition comprising:
an anticalculus agent; and
a *Magnolia* antibacterial agent;

wherein the composition is free of phosphate-containing anticalculus agents and polyphosphate-containing anticalculus agents; and wherein the anticalculus agent comprises zinc oxide, wherein the *Magnolia* antibacterial agent is at least one selected from the group consisting of magnolol, honokiol, tetrahydromagnolol, tetrahydrohonokiol, propylmagnolol, propylhonokiol, isopropylmagnolol, isopropylhonokiol, butylmagnolol, and butylhonokiol.

2. The oral care composition of claim 1, wherein the *Magnolia* antibacterial agent comprises magnolol.

3. The oral care composition according to claim 1, wherein the composition further comprises sodium sulphate and sodium lauryl sulphate.

4. The oral care composition according to claim 1, wherein the composition comprises at least 1.6% by weight of sodium lauryl sulphate.

5. The oral care composition according to claim 1, wherein the oral care composition is a dentifrice.

6. A method for treating or preventing calculus formation in the oral cavity, which comprises contacting the oral cavity with the oral care composition of claim 1.

7. A method of inhibiting oral uptake of a *Magnolia* antibacterial agent from an oral care composition of claim 1 comprising formulating the oral care composition by combining zinc oxide and said *Magnolia* antibacterial agent, without phosphate-containing anticalculus agents or polyphosphate-containing anticalculus agents.

* * * * *